United States Patent [19]
Perkins et al.

[11] Patent Number: 6,083,195
[45] Date of Patent: Jul. 4, 2000

[54] OPHTHALMIC ASPIRATION SYSTEM WITH SELECTABLE VENT METHOD

[75] Inventors: James T. Perkins, St. Charles County; Jeffery A. Knight; William J. Neubert, both of St. Louis County, all of Mo.

[73] Assignee: Bausch & Lomb Surgical, Inc., Claremont, Calif.

[21] Appl. No.: 09/173,451

[22] Filed: Oct. 15, 1998

[51] Int. Cl.[7] .............................. A61M 1/00; A61M 35/00
[52] U.S. Cl. .................. 604/30; 604/35; 604/294
[58] Field of Search .................. 604/30, 35, 45, 604/65, 129, 246, 247, 500, 294, 320; 606/162

[56] References Cited

U.S. PATENT DOCUMENTS

| | | |
|---|---|---|
| 4,117,843 | 10/1978 | Banko . |
| 4,773,897 | 9/1988 | Scheller et al. . |
| 4,935,005 | 6/1990 | Haines . |
| 5,267,956 | 12/1993 | Beuchat . |
| 5,580,347 | 12/1996 | Reimels ................................ 604/30 |
| 5,746,719 | 5/1998 | Farra et al. . |
| 5,897,524 | 4/1999 | Wortrich et al. ........................ 604/30 |

*Primary Examiner*—Mark O. Polutta
*Assistant Examiner*—Michael J Hayes
*Attorney, Agent, or Firm*—Grant D. Kang

[57] ABSTRACT

An ophthalmic irrigation/aspiration system that permits selection among or between various venting modes.

1 Claim, 1 Drawing Sheet

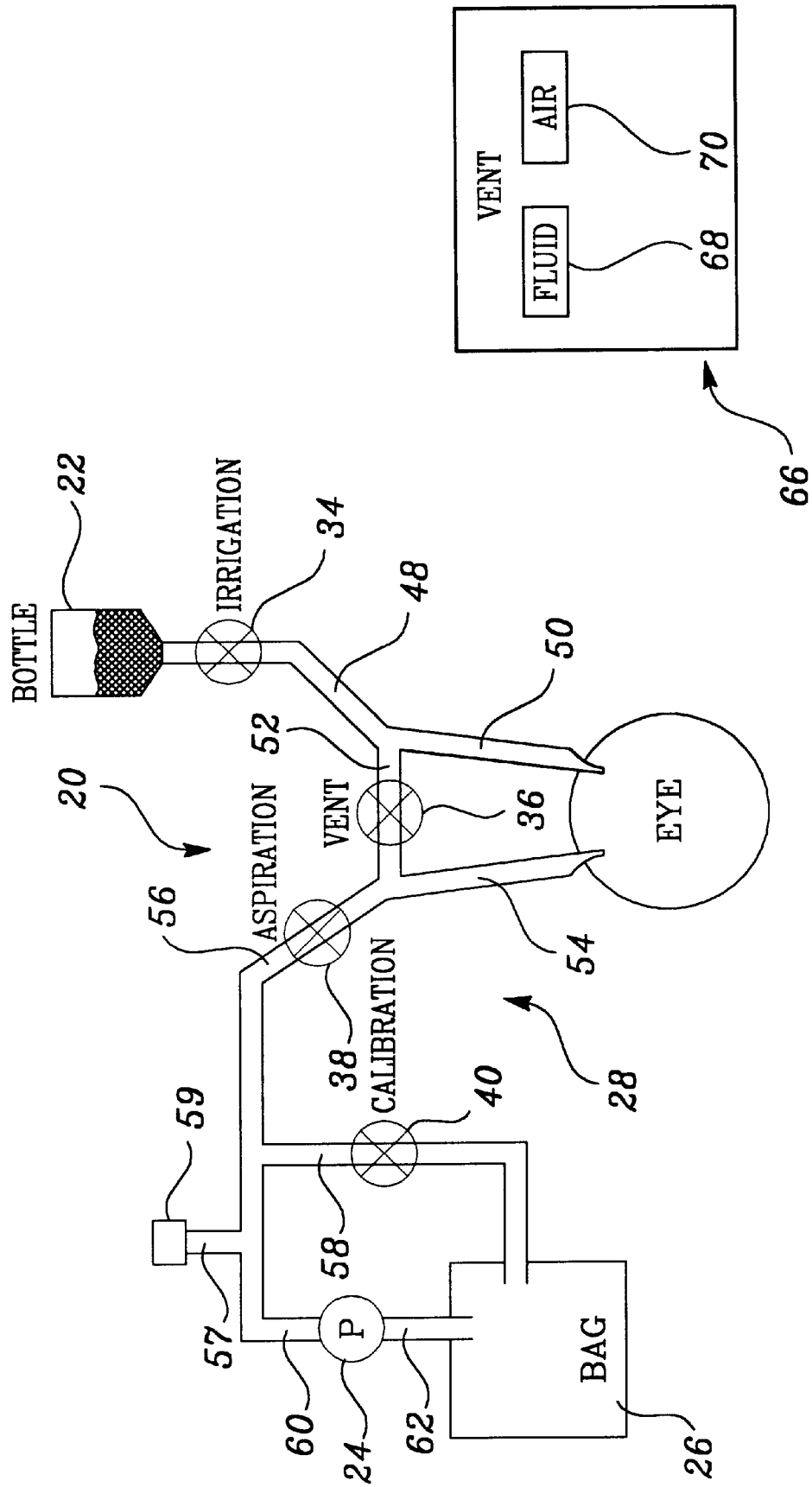

OPHTHALMIC ASPIRATION SYSTEM WITH SELECTABLE VENT METHOD

BACKGROUND OF THE INVENTION

1. Field of the Invention

This invention relates to an ophthalmic irrigation and aspiration system and, more particularly, to venting in an ophthalmic aspiration system.

2. Related Art

All ophthalmic irrigation and aspiration systems currently on the market provide only one means for venting. The term "venting" refers to the common practice of reducing or eliminating a vacuum or pressure differential between components of an irrigation/aspiration system, or between the irrigation/aspiration system and ambient atmosphere pressure.

The term "fluid venting" refers to the reduction of pressure differentials between the portion of the aspiration circuit that contacts the eye and remainder of the aspiration circuit by way of a connection between the irrigation fluid path and the aspiration path. The term "air venting" or "atmospheric venting" refers to the reduction of pressure differentials between the portion of the aspiration circuit that contacts the eye and remainder of the aspiration circuit by way of a connection between the aspiration path and ambient air at atmospheric pressure.

In ophthalmic irrigation/aspiration systems that utilize a peristaltic pump, fluid venting is the most commonly used method. For example, the Legacy microsurgical system sold by Alcon Laboratories uses fluid venting in its peristaltic-pump-based irrigation/aspiration system. No other type of venting is utilized in this system.

In some peristaltic systems, such as that commercialized by AMO, venting is accomplished through pump reversal.

For venturi aspiration systems, such as that commercialized by Bausch & Lomb Surgical in its Phacotron Gold product and in its Storz Millennium Microsurgical System product, air venting is used.

All ophthalmic aspiration systems currently in commercial use have a single method or option for venting with no opportunity for selection.

Accordingly, there is a need in the art to provide an ophthalmic aspiration system that provides the ability to select, either manually or automatically, among or between various methods of venting in an ophthalmic aspiration system.

SUMMARY OF THE INVENTION

It is in view of the above problems that the present invention was developed. The invention is an ophthalmic aspiration system that provides the ability to select, either manually or automatically, among or between various methods or options of venting. In addition, the invention provides the ability to vent using a combination of venting options or methods employed simultaneously. The selection may be made using an electronic switch, graphical user interface, electronically-controlled electromechanical devices and other commonly employed selection means.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 1 illustrates an ophthalmic irrigation/aspiration system of the present invention; and FIG. 2 illustrates a user interface for selecting a venting option or method.

DETAILED DESCRIPTION OF THE PREFERRED EMBODIMENTS

Referring to the accompanying drawings in which like reference numbers indicate like elements, FIG. 1 illustrates an ophthalmic irrigation/aspiration system shown generally at 20 that is configured for use with a positive displacement, scroll pump. Ophthalmic irrigation/aspiration system 20 comprises bottle 22, pump 24, and bag 26 all connected by hydraulic circuit shown generally at 28.

Irrigation pinch valve 34, vent pinch valve 36, aspiration pinch valve 38, and air venting or calibration pinch valve 40 are disposed at various locations within hydraulic circuit 28. An eye is shown generally at 44.

During normal irrigation and aspiration, irrigation pinch valve 34 is in an open position, vent pinch valve 36 is in a closed position, aspiration pinch valve 38 is in an open position, and calibration pinch valve 40 is in a closed position.

Hydraulic circuit 28 includes first section 48, second section 50, third section 52, fourth section 54, fifth section 56, transducer interface 57, transducer 59, sixth section 58, seventh section 60, and eighth section 62.

Accordingly, when pump 24 is in operation, fluid is pulled from bottle 22, through first section 48 and second section 50 into eye 44. Fluid is removed from eye 44 by the suction from pump 24 through fourth section 54, fifth section 56, seventh section 60, through pump 24, through eighth section 62 to bag 26.

In FIG. 2, a user interface 66 for selecting a venting option is illustrated. A window display is provided with a "vent" legend in the upper center of the window. A fluid button 68 or an air button 70 may be selected. When a user presses fluid button 68, fluid venting is selected. When fluid venting is selected, pump 24 is stopped and vent pinch valve 36 is opened. As a result, the vacuum developed in fifth section 56 and seventh section 60 draws fluid from bottle 22 through first section 48 and through third section 52. In this instance, fluid from the bottle 24 is used to vent the vacuum developed by pump 24. In the preferred embodiment, aspiration pinch valve 38 closes, vent pinch valve 36 and calibration pinch valve 40 open, and irrigation pinch valve 34 remains open until vacuum transducer 59 senses less than 15 mm of mercury vacuum. When this condition occurs, the vacuum has essentially abated and three pinch valves, 34, 36, and 38, may be closed, and 40 remains open.

With ophthalmic irrigation/aspiration system 20, fluid motor reversal venting may also be accomplished. To accomplish fluid motor reversal venting from the irrigation/aspiration 20 mode, pump 24 is stopped and then reversed. None of the pinch valves, 34, 36, 38, and 40, change position. Then pump 24 is run in full reverse until a pressure transducer 59 senses the existence of less than 15 mm of mercury vacuum. At that point, the motor is stopped.

Referring again to FIG. 2, air button 70 may be selected in lieu of fluid button 68. Accordingly, air venting is selected. As a result, ophthalmic irrigation/aspiration system 20 switches from an irrigation/aspiration mode to an air venting mode. To accomplish air venting, pump 24 is stopped. Irrigation pinch valve 34 is open, vent pinch valve 36 is closed, aspiration pinch valve 38 is open, and calibration pinch valve 40 is open. Again, as with any venting scheme, the purpose is to relieve a vacuum pressure developed in fourth section 54, fifth section 56, sixth section 58, transducer interface 57, and seventh section 60. Accordingly, with the opening of calibration pinch valve 40, the vacuum developed pulls air from bag 26 through sixth section 58. Any fluid in sixth section 58 distributes into fourth section 54, fifth section 56, sixth section 58, transducer interface 57, and seventh section 60, thereby relieving the pressure developed in those sections. Additional information is provided in a co-pending application Ser. No. 09/173/452, filed Oct. 15, 1998, and titled Fluid Venting in Ophthalmic Irrigation/Aspiration System filed by inventors James Perkins and Jeffery Knight; and further in a co-pending application Ser. No. 09/173/453, filed Oct. 15, 1998, and titled Air Venting in Ophthalmic Irrigation/Aspiration System Via Closed Bag System filed by inventors James Perkins, William Neubert, and Jeffery Knight; both applications are hereby incorporated by reference in their entirety.

As a result, an invention has been described that provides the ability to vent using a combination of venting options. It should be noted that user interface 66 may be graphical in nature such as a touchscreen. Alternatively, it maybe an electronically-controlled electro-mechanical device such as an electromechanical button with a physical travel. In addition, user interface 66 may be an electronic switch.

Pinch valves 34, 36, 38, and 40 are electronically-controlled electromechanical devices that are well-known in the art.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An ophthalmic aspiration system comprising:

an irrigation circuit for conveying fluid from a bottle to an irrigation distal end and into a patient's eye;

an aspiration circuit interconnected with the irrigation circuit and for conveying fluid from the patient's eye to a collection bag;

a pump forming a part of the aspiration circuit and connected between the collection bag and an aspiration distal end;

an aspiration pinch valve located between the pump and the aspiration distal end;

an irrigation pinch valve located between the bottle and the irrigation distal end;

a fluid venting valve located between the irrigation circuit and the aspiration circuit;

an air venting valve and circuit connected to the bag and the aspiration circuit; and whereby coordinated operation of each of the aspiration pinch valve, the irrigation pinch valve, the fluid venting valve, and the air venting valve results in fluid venting, air venting, or a combination of fluid and air venting.

* * * * *